United States Patent
Bae et al.

(10) Patent No.: US 8,273,953 B2
(45) Date of Patent: Sep. 25, 2012

(54) ANTISENSE DNA OF SWEETPOTATO EXPANSIN CDNA AND METHOD FOR INCREASING STORAGE ROOT YIELD USING THE SAME

(75) Inventors: Jung Myung Bae, Seoul (KR); Seol Ah Noh, Seoul (KR); Jeong Sheop Shin, Seoul (KR); Kyung Hee Paek, Seoul (KR)

(73) Assignee: Korea University Industrial & Academic Collaboration Foundation, Seoul (KR)

(*) Notice: Subject to any disclaimer, the term of this patent is extended or adjusted under 35 U.S.C. 154(b) by 558 days.

(21) Appl. No.: 12/373,090

(22) PCT Filed: Mar. 10, 2008

(86) PCT No.: PCT/KR2008/001343
§ 371 (c)(1),
(2), (4) Date: Jan. 9, 2009

(87) PCT Pub. No.: WO2008/111779
PCT Pub. Date: Sep. 18, 2008

(65) Prior Publication Data
US 2009/0249515 A1  Oct. 1, 2009

(30) Foreign Application Priority Data
Mar. 13, 2007  (KR) .................. 10-2007-0024730

(51) Int. Cl.
C12N 15/113 (2010.01)
C12N 15/29 (2006.01)
C12N 15/82 (2006.01)
(52) U.S. Cl. ...................... 800/290; 800/266
(58) Field of Classification Search ........... 800/278–298
See application file for complete search history.

(56) References Cited

U.S. PATENT DOCUMENTS

| | | |
|---|---|---|
| 7,001,743 B2 | 2/2006 | Cosgrove et al. |
| 7,217,861 B2 | 5/2007 | Lee et al. |
| 2003/0054533 A1 | 3/2003 | Cosgrove et al. |
| 2003/0167506 A1* | 9/2003 | Multani et al. ............... 800/278 |
| 2004/0049809 A1 | 3/2004 | Fonseca et al. |
| 2005/0246795 A1 | 11/2005 | Lee et al. |

OTHER PUBLICATIONS

Gama et al., Plant Cell Tis. Org. Cult., 1996, vol. 46, pp. 237-244.*
Kwasniewski, M. et al., Plant Physiology, "Molecular cloning and characterization of β-expansin gene related to root hair formation in barley," vol. 141, 1149-1158 (2006).
Lin, Z., et al., Mol. Gen. Genomics, "Isolation and characterization of 18 genes encoding α- and β-expansins in wheat (*Triticum aestivun* L.)," vol. 274: 548-556 (2005).
Lee, D.K., et al., Plant Physiology, "Expression of an expansin gene is correlated with root elongation in soybean," vol. 131, 985-997 (2003).
Sampedro, J., et al., Genome Biology, "The expansin superfamily," vol. 6: 242 (2005).
Dotto, M.C., et al., Plant Physiology Biochemistry, "Expression of expansin genes in strawberry varieties with contrasting fruit firmness," vol. 44 (5-6): 301-307 (2006).
Muller, B., et al., Plant Physiology, "Association of specific expansins with growth in maize leaves is maintained under environmental, genetic, and developmental sources of variation," vol. 143(1): 278-290 (Epub 2006).
Fan, L., et al., Plant Physiology, "Progressive inhibition by water deficit of cell wall extensibility and growth along the elongation zone of maize roots is related to increased lignin metabolism and progressive stelar accumulation of wall phenolics," vol. 140 (2): 603-612 (Epub 2005).

* cited by examiner

*Primary Examiner* — Russell Kallis
(74) *Attorney, Agent, or Firm* — Sughrue Mion, PLLC

(57) ABSTRACT

Disclosed herein are antisense DNA of a sweetpotato expansin (IbExpansin) cDNA, a plant transformation vector carrying the same, and a method for increasing storage root production using the same. The transgenic sweetpotatoes prepared using the antisense DNA of IbExpansin cDNA have storage root production increased by up to one and half times. Thus, the gene is useful in the generation of highly productive transgenic storage roots for the increase of bioethanol production.

4 Claims, 9 Drawing Sheets

Figure 4

| | | | |
|---|---|---|---|
| SEQ ID NO: 18 | PcExpansin : | ---------MK AIAYGF CLVGLLA VSCA AYGGGG VNA ATFYGG DASGTMGGACG | : 51 |
| SEQ ID NO: 19 | PpExpansin : | ---------MK AIAYGF CLVGLLA VSCA AYGGGG VNA ATFYGG DASGTMGGACG | : 51 |
| SEQ ID NO: 20 | PaExpansin : | ---------MK AIAYGF CLVGLLA VSCA AYGGGG VDA ATFYGG DASGTMGGACG | : 51 |
| SEQ ID NO: 21 | CaExpansin : | ----------MALLG-LL MGISL FQSV GYGG--W NA ATFYGG DASGTMGGACG | : 46 |
| SEQ ID NO: 22 | LeExpansin : | ----------MALLA-IL MGISL FQSA GYGG--W NA ATFYGG DASGTMGGACG | : 46 |
| SEQ ID NO: 23 | IbExpansin : | HSSTNSTEAIT AVLE-LLLVGV ATL SPV GYWG--W SSA ATFYGG DASGTMGGACG | : 57 |

PcExpansin : YGNLYSQGYGTNTAALSTALFNNGLGCGSCYEIRCV DPK CLP AIVV IATNFCPP NA : 111
PpExpansin : YGNLYSQGYGTNTAALSTALFNNGLGCGSCYEIRCV SDPK CLP AIVV IATNFCPP NNA : 111
PaExpansin : YGNLYSQGYGTNTAALSTALFNNGLGCGSCYEIRCV DPK CLP AIVV IATNFCPP NNA : 111
CaExpansin : YGNLYSSGYGTNTAALSTALFNNGLSCGQCFQLMCV ARQ CLP GIII VIATNFCPP--- : 103
LeExpansin : YGNLYSTGYGTNTAALSTALFNNGLSCGACFQLMCV AGQ CLP GIII VIATNFCPP--- : 103
IbExpansin : YGNLYSSGYGTNTAALSTALFNNGLSCGSCFQIRCV D-RSCLR GVI VIATNFCPP--- : 113

PcExpansin : LPNRAGGWCNPPQ HEDLSQPVFQ IAQYKAGVVPVAYRRVPCRR GGIRFTINGHSYFN : 171
PpExpansin : LPNRAGGWCNPPQ HEDLSQPVFQ IAQYKAGVVPVAYRRVPCRR GGIRFTINGHSYFN : 171
PaExpansin : LPNRAGGWCNPPQ HEDLSQPVFQ IAQYKAGVVPVAYRRVPCRR GGIRFTINGHSYFN : 171
CaExpansin : -----GGWCDPPN HEDLSQPIFL RIAQYRAGIVPVAYRRVPCRR GGIRFTINGHSYFN : 158
LeExpansin : -----GGWCDPPR P HEDLSQPIFL RIAQYRAGIVPVAYRRVPCRRSGGIRFTINGHSYFN : 158
IbExpansin : -----GGWCEPPN P HEDLSQPVFL RIAQYRAGVVPVAYRRVPCRRSGGIRFTINGHAFFN : 168

PcExpansin : LVLITNVGGAGDVHSVSVKGSRTG WQ MSRHWGQNWQS S LNGQSLSFFVTTSDGRTVV : 231
PpExpansin : LVLITNVGGAGDVHSVSVKGSRTG WQ MSRHWGQNWQS S LNGQSLSFFVTTSDGRTVV : 231
PaExpansin : LVLITNVGGAGDVHSVSVKGSRTG WQ MSRHWGQNWQS S LNGQSLSFFVTTSDGRTVV : 231
CaExpansin : LVLVTNVGGSGDVHSVVIKGSRTQ WQ MSRHWGQNWQN A LNGQSLSFFVTTGDGRTVV : 218
LeExpansin : LVLVTNVGGSGDVHSVVIKGSRTQ WQ MSRHWGQNWQN A LNGQSLSFFVTTGDGRTVV : 218
IbExpansin : LVLVTNVGGSGDV A VVIKGSRTG WQ MSRHWGQNWQS ANL NGQSLSFFVVTGDSRSVV : 228

PcExpansin : AYRAAP AG WSFGQTYSC QFR : 252
PpExpansin : SYRAAP AG WSFGQTYSC QFR : 252
PaExpansin : SYRAAP AG WSFGQTYSC QLR : 252
CaExpansin : SYRAAP SS WSFGQTFSC GQR : 239
LeExpansin : SYRAAP SS WSFGQTFSC GQR : 239
IbExpansin : SYRAAP P CWSFGQTYSC AQR : 249

PcExpansin – 'Prunus cerasus'
PpExpansin – 'Prunus persica'
PaExpansin – 'Prunus avium'
CaExpansin – 'Capsicum annuum'
LeExpansin – 'Lycoperson esculentum'
IbExpansin – 'Ipomoea batatas'

Figure 5

Homology among expansin amino acid sequences

| Sequence comparison | | Identity (%) |
|---|---|---|
| | | overall |
| IbExpansin | LeExpansin | 78 |
| | CaExpansin | 79 |
| | PcExpansin | 73 |
| | PaExpansin | 73 |
| | PpExpansin | 73 |

Figure 6

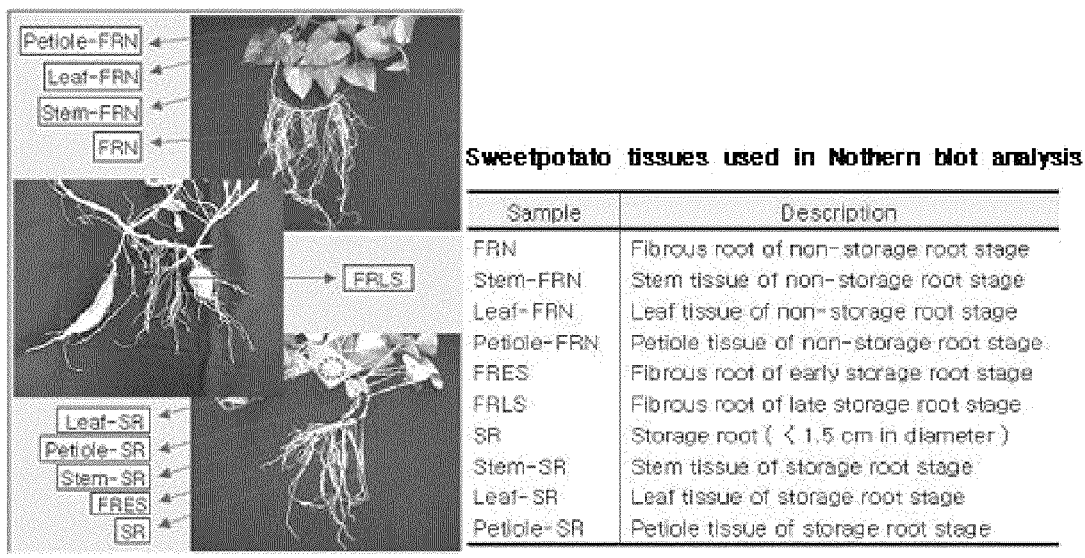

Sweetpotato tissues used in Nothern blot analysis

| Sample | Description |
|---|---|
| FRN | Fibrous root of non-storage root stage |
| Stem-FRN | Stem tissue of non-storage root stage |
| Leaf-FRN | Leaf tissue of non-storage root stage |
| Petiole-FRN | Petiole tissue of non-storage root stage |
| FRES | Fibrous root of early storage root stage |
| FRLS | Fibrous root of late storage root stage |
| SR | Storage root ( < 1.5 cm in diameter ) |
| Stem-SR | Stem tissue of storage root stage |
| Leaf-SR | Leaf tissue of storage root stage |
| Petiole-SR | Petiole tissue of storage root stage |

Expression Pattern of IbExpansin

Kpn I/BamH I digestion         Colony PCR         Kpn I/BamH I digestion

Figure 9
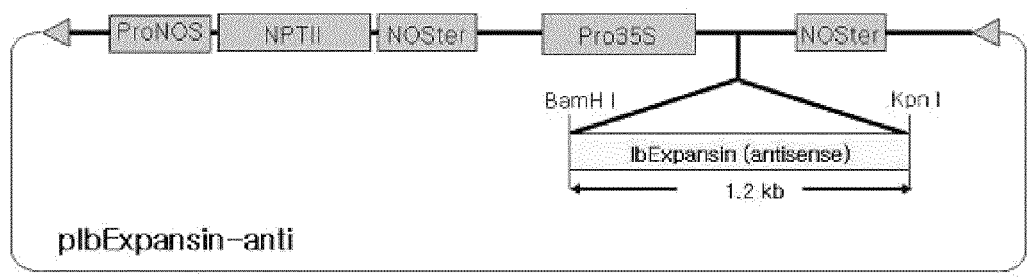
Figure 10
In vitro cultured sweetpotato
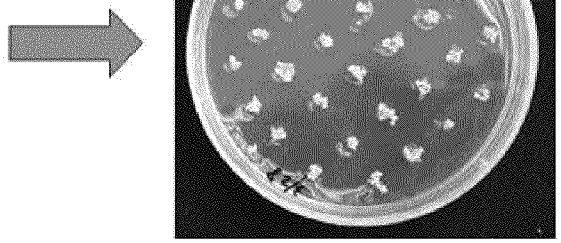
Sweetpotato embryogenic callus

|  | Storage root | | Shoot | |
| --- | --- | --- | --- | --- |
|  | Number | Total weight (g) | Number | Total weight (g) |
| Wild-type | 4.75±0.96 | 163.71±24.62 | 2.5±0.58 | 118.13±19.02 |
| antisense1 | 5.33±0.58 | 248.20±33.93 | 3.3±0.58 | 118.48±11.66 |
| antisense4 | 8.25±1.50 | 224.45±30.55 | 2.8±0.75 | 118.48±11.02 |

ANTISENSE DNA OF SWEETPOTATO EXPANSIN CDNA AND METHOD FOR INCREASING STORAGE ROOT YIELD USING THE SAME

This is a National Stage under 35 U.S.C. §371 of PCT/KR2008/001343 filed on Mar. 10, 2008, which claims priority from Korean patent application 10-2007-0024730 filed on Mar. 13, 2007, all of which are incorporated herein by reference.

TECHNICAL FIELD

The present invention relates to an antisense DNA of sweetpotato expansin cDNA useful in the generation of highly productive storage roots. More particularly, the present invention relates to an antisense DNA of sweetpotato expansin cDNA, a transformation vector carrying the same, and a method for increasing storage root production using the same.

BACKGROUND ART

Since the discovery of expansin by Cosgrove and his colleagues (McQueen-Mason et al., 1992, Plant Cell 4, 1425-1433), intensive studies have been conducted thereon. In early studies, expansins were known as cell-wall-loosening enzymes that mediate, at least in part, pH-dependent extension of the plant cell wall and the growth of the cell (Cosgrove, 2000, Nature 407, 321-326). Since then, expansins were found to be in either α- or β-form (Shcherban et al., 1995, PNAS 92, 9245-9249).

More recently, expansins have been found to be involved in regulating, besides cell expansion, a variety of other plant processes, including morphogenesis (Ruan et al., 2001, Plant Cell 13, 47-60), softening of fruits (Rose et al., 2000, Plant Physiology 123, 1583-1592; Civello et al., 1999, Plant Physiology 121, 1273-1280), growth of the pollen tube (Cosgrove et al., 1997, PNAS 94, 6559-6564), elongation of graviresponding roots (Zhang and Hasenstein, 2000, Plant Cell Physiology 41, 1305-1312), and elongation of root cells (Lee et al., 2003, Plant Physiology 131, 985-997) (for review, Lee et al., 2001, Cur. Opin. Plant Biol. 4, 527-532).

Further, the expression pattern of expansins in flooded rice and tomatoes has been well studied. It has been found that expansins are expressed in the shoot apical meristem of tomato for incipient leaf primordium initiation (Reinhardt et al., 1998, Plant Cell 10, 1427-1437). An expansin gene (Exp1) was cloned and found through transformants therewith to play an important role in the growth and ripening of tomato fruits in (Brummell et al., 1999, Plant Cell, 11: 2203-2216). Expansin mRNA was accumulated just before the rate of growth or the loosening degree of the cell wall started to increase, suggesting that the expression of expansin genes is correlated with cell elongation (Cho and Kende, 1997a, Plant Cell 9, 1661-1671; 1997b, Plant Physiology 113, 1137-1143; 1998, Plant Journal 15, 805-812). Transgenic rice plants in which expansins are overexpressed were observed to further increase the length of cotyledons by 31-97% compared with the wild type (Choi et al., 2003 Plant Cell, 15: 1386-1398). However, the transgenic rice plants are unable to bear seeds due to male sterility.

On the other hand, sweetpotato storage roots are a good energy source for people because they contain a lot of starch and various kinds of inorganic nutrients, and are high value-added crops having beneficial health effects owing to their high content of fiber, which is a material useful in the body.

Recently, as bio-ethanol obtained upon the fermentation of plants comes into the spotlight as an alternative energy source, sweetpotato storage roots are also being considered as a useful alternative energy crop.

It is very important to increase the productivity per unit area under cultivation of alternative energy crops in view of enhancing the price competitiveness of alternative energy.

Further, there has been little research on the molecular mechanisms of storage root production because the material of the storage root is not suitable for molecular study, for the following reasons: (1) it is not easy to extract DNA and RNA because of the large amounts of polysaccharide; and (2) it is not easy to monitor storage root growth because the storage root grows in the ground, and thus studies into molecular breeding to regulate the development of sweetpotato storage root have been limited.

Therefore, there has been a need for molecular breeding to regulate the development of sweetpotato storage root and transgenic sweetpotato that can remarkably increase production using the molecular breeding.

DISCLOSURE

Technical Problem

Accordingly, the present invention has been made keeping in mind the above problems occurring in the prior art, and an object of the present invention is to provide an antisense DNA of sweetpotato expansin (IbExpansin) cDNA with which highly productive transgenic sweetpotato can be prepared.

It is another object of the present invention to provide a method for increasing storage root production by suppressing the expression of expansin using the antisense DNA of IbExpansin cDNA.

It is a further object of the present invention to provide a highly productive transgenic sweetpotato which comprises a vector carrying the antisense DNA of IbExpansin cDNA.

Technical Solution

In order to accomplish the objects, therefore, the present invention provides a method for increasing storage root production, comprising suppressing the expression of an expansin gene in cells of a plant.

According to the preferred embodiment of the present invention, the method further comprises introducing antisense DNA of a cDNA from a sweetpotato expansin gene (IbExpansin) into the plant.

According to the preferred embodiment of the present invention, the method further comprises inserting an antisense DNA of the expansin gene into a binary vector, and introducing the binary vector into the plant.

The antisense DNA comprises a nucleotide sequence of SEQ ID NO.: 9.

The plant is sweetpotato.

According to another aspect of the present invention, the present invention provides a method for preparing highly productive transgenic sweetpotato, comprising introducing antisense DNA of a sweetpotato expansin cDNA into sweetpotato.

According to another aspect of the present invention, the present invention provides a PCR primer suitable for amplifying a DNA fragment comprising the nucleotide sequence of SEQ ID NO.: 9, said primer being represented by one of the nucleotide sequences as shown in SEQ ID NO. 10 or 11.

Advantageous Effects

The present invention provides an antisense DNA of IbExpansin cDNA (expansin cDNA derived from *Ipomoea bata-*

*tas*) that is useful for transforming plants, and the resulting transgenic plants are capable of accelerating the growth of storage root by suppressing the elongation growth of roots. Therefore, the present invention is useful in the generation of highly productive transgenic storage root.

DESCRIPTION OF DRAWINGS

The above and other objects, features and other advantages of the present invention will be more clearly understood from the following detailed description taken in conjunction with the accompanying drawings, in which:

FIG. 4 shows a comparison of the amino acid sequence of the sweetpotato expansin cDNA (SEQ ID NO: 23) with amino acid sequences of other plant expansin cDNA (SEQ ID NO: 18-22);

FIG. 5 shows amino acid sequence homologies between the sweetpotato expansin cDNA and other plant expansin cDNA;

FIG. 6 shows sweetpotato tissues used in examining expression patterns of sweetpotato expansin gene;

FIG. 9 is a schematic diagram showing the structure of a pIbExpansin-anti binary vector for carrying the antisense DNA of sweetpotato expansin cDNA of the present invention into sweetpotatoes;

FIG. 10 shows embryogenic callus induced in sweetpotato for transferring the antisense DNA of sweetpotato expansin cDNA of the present invention into sweetpotatoes;

BEST MODE

Hereinafter, the preferred embodiment of the present invention will be described with reference to the accompanying drawings.

First, the present inventors succeeded in cloning a sweetpotato expansin (IbExpansin) cDNA, constructing a binary vector suitable for plant transformation using the antisense DNA of the cDNA, and transforming the vector into sweetpotato. The transgenic sweetpotato was found to significantly increase storage root production.

Therefore, the present invention provides an antisense DNA of sweetpotato expansin cDNA, comprising a nucleotide sequence of SEQ ID NO.: 9.

The antisense DNA of the cDNA has a nucleotide sequence 1,213 bp long.

Further, the present invention provides a binary vector (pIbExpansin-anti) for transforming plants, carrying the antisense DNA of sweetpotato (*Ipomoea batatas*) expansin cDNA (IbExpansin).

The plant transformation vector is a binary vector capable of stably expressing an exogenous gene of interest in plants.

In a pMBP1 vector, the antisense DNA of sweetpotato expansin cDNA (IbExpansin) according to the present invention is located between a CaMV35S promoter and an NOS terminator. It should be understood by those skilled in the art that any other plant transformation vector can be used instead of the pMBP1 vector.

Further, the present invention provides a transgenic sweetpotato carrying the antisense DNA of sweetpotato expansin cDNA (IbExpansin) according to the present invention on a binary vector.

The binary vector may be introduced into plants using Agrobacterium or a gene gun. In an embodiment of the present invention, a gene gun method (Sanford etc, 1993) was used for transforming sweetpotato.

In addition to sweetpotato, the antisense DNA of sweetpotato expansin cDNA (IbExpansin) according to the present invention may be introduced into any plant storage root which is adapted to have increased storage root production.

Further, the present invention provides a pair of primers for the PCR amplification of the antisense DNA of sweetpotato expansin cDNA (IbExpansin) according to the present invention, which is represented by SEQ ID NO.: 10 and SEQ ID NO.: 11.

Further, the present invention provides a method for increasing storage root production by suppressing the expression of an expansin gene using the antisense DNA of the expansin cDNA.

Further, the present invention provides a method for increasing storage root production by inserting an antisense DNA of the expansin cDNA into a binary vector, and introducing the binary vector into the plant.

As mentioned above, some of the expansin family genes are disclosed, but nowhere has the application of expansin genes for storage root production increase been mentioned in reports predating the present invention. In accordance with the present invention, antisense DNAs of various expansin cDNAs can be introduced into plants in order to increase their storage root production.

EXAMPLE 1

Cloning of Sweetpotato Expansin cDNA

Figure 1:
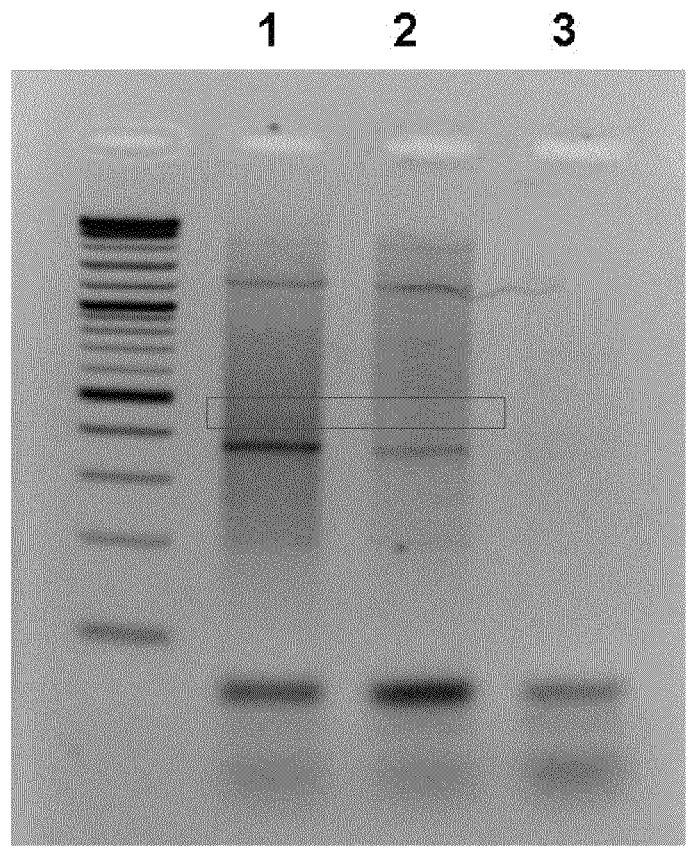
FIG. 1 is a view showing the results of primary PCR for cloning a full-length sweetpotato expansin cDNA.

Total RNA was isolated from a fresh tuber of sweetpotato and was used to construct an EST (Expressed Sequence Tag) library. Using this library, 2,859 ESTs were cloned and deposited in the National Center for Biotechnology Information (NCBI) with NCBI Accession Nos.: BU690119-BU692977 (You et al., 2003, FEBS Letters 536, 101-105). Of them, IbExpansin (NCBI Accession No. BU691452) was found to be about 1 kb long, and was identified as a partial cDNA devoid of the start codon ATG. To obtain full length IbExpansin, PCR was performed in the presence of an IbExpansin-specific primer (SEQ ID NO.: 3) and a T3 vector primer, with the preexisting EST library of early sweetpotato storage root development serving as a template. However, no bands were visible at the position of the expected 5' full length size (FIG. 1).

Figure 2:
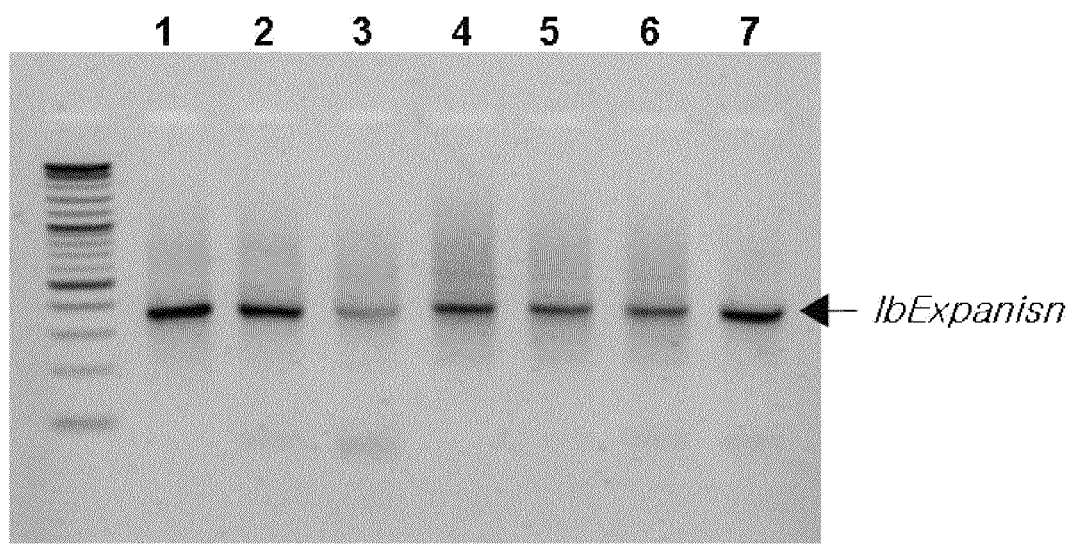
FIG. 2 is a view showing the results of secondary PCR for cloning a full-length sweetpotato expansin cDNA, with the primary PCR product serving as a template.

DNA fragments were eluted from a gel piece excised from the agarose gel at the expected full length position and used as a template for PCR, with a set of a gene-specific nested primer (SEQ ID NO.: 4) and a T3 primer. As a result, a PCR product having a length of about 350 bp was obtained (FIG. 2).

The PCR product was inserted into a pGEM-T Easy vector for sequencing analysis and identified 5' sequence of IbExpansin.

Figure 3:
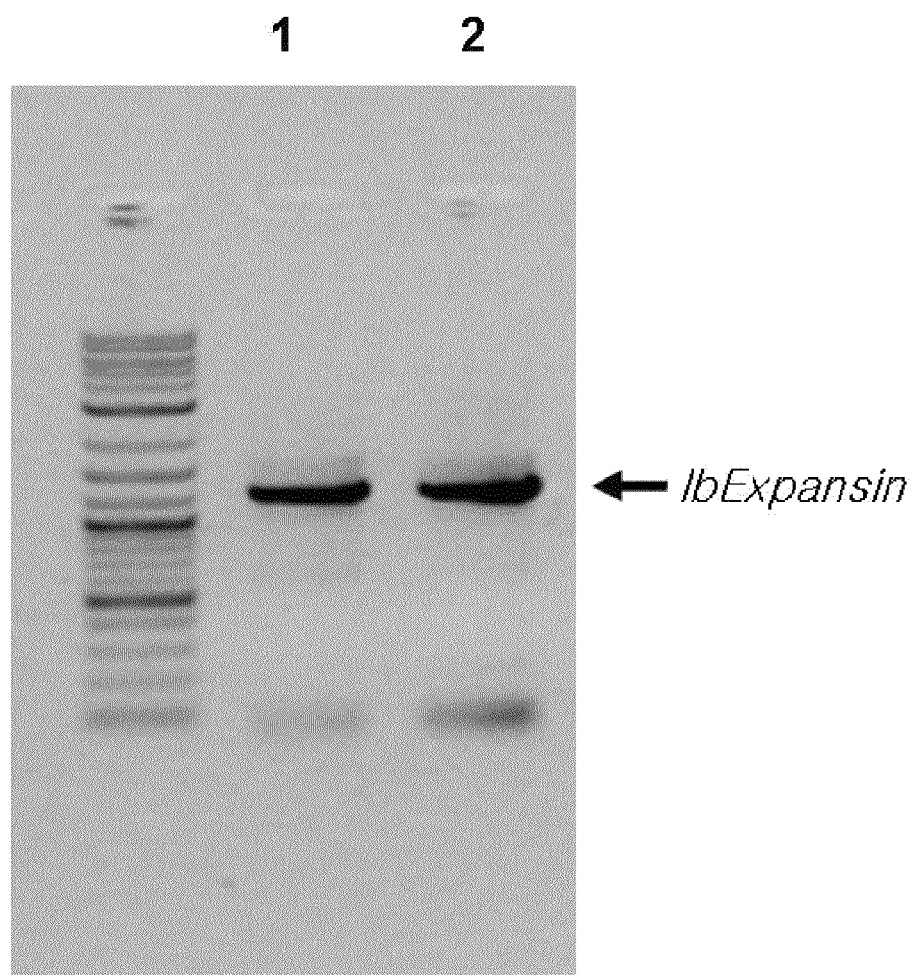
FIG. 3 is a view showing the full-length sweetpotato expansin cDNA cloned by PCR in accordance with the present invention.

On the basis of the nucleotide sequence, 5' and 3' primers were synthesized with BamHI and KpnI restriction sites provided respectively to their termini. RT-PCR was performed with the primers to obtain a full-length IbExpansin (FIG. 3).

EXAMPLE 2

Sequencing and Analysis of Nucleotide Sequence of Full-Length IbExpansin

A 1.2 kb full-length cDNA was cloned by PCR and inserted into a pGEM-T Easy vector, which was then amplified. Sequencing analysis revealed that IbExpansin is 1,213 bp long and consists of a 33 bp 5'-UTR, a 717 bp ORF, and a 463 bp 3'-UTR. This full-length IbExpansin cDNA was registered in NCBI, with Accession No.: DQ515800. The IbExpansin amino acid sequence, consisting of 238 amino acid residues, is highly conserved, with the exception of the N-terminal region (FIG. 4), and shares homology as high as 78% with expansin amino acid sequences of tomato and pepper (FIG. 5).

EXAMPLE 3

Northern Blot Analysis of Tissues

1. Northern blotting

The expression pattern of IbExpansin was examined with various tissues at various developmental stages through Northern blotting.

For the isolation of total RNA, roots, stems, leaves and petioles of sweetpotato at various developmental stages were used as RNA sources. That is, total RNA was isolated from tissues in a non-storage root stage, such as roots (FRN: fibrous root in non-storage root stage), stems (stem-FRN), leaves (Leaf-FRN) and petioles (petiole-FRN); tissues in an early storage root stage, such as roots (fibrous root in early storage root stage, FRES); tissues in a storage root stage, such as roots (SR), stems (Stem-SR), leaves (Leaf-SR) and petioles (Petiole-SR); and tissues in a late storage root stage, such as roots (fibrous root in late storage root stage, FRLS) (FIG. 6). Total RNA extraction was performed using a 4.4 M guanidinium-SDS lysis buffer (Chirgwin et al., 1979)/5.7 M CsCl gradient method (Glisin et al., 1974). About 20 μg of the extracted total RNA was electrophoresed on 1% agarose-formaldehyde gel and transferred onto a Tropilon-plus™ nylon membrane (Tropix, USA).

A probe was obtained by amplification from 2.5 ng of a plasmid carrying a 1 kb Expansin EST clone through PCR, which was performed in a PCR mixture containing 100 μM of dNTP mix exclusive of dCTP, 100 μM of dCTP-biotin, 10 μM of vector (pBluescript II) primers T3 (5'-AATTAACCCT-CACTAAAGGG-3'; SEQ ID NO.: 7) and T7 (3'-CGG-GATATCACTCAGCATAATG-5'; SEQ ID NO.: 8) each, 1×PCR buffer, and 1 unit of Taq polymerase to a final volume of 10 μl, starting with pre-denaturation at 95° C. for 5 min before 35 cycles of denaturation at 95° C. for 10 sec, annealing at 65° C. for 30 sec and extension at 72° C. for 30 sec.

The PCR-amplified biotinylated probe was purified using a QIAquick™ PCR purification kit (QIAGEN, Germany) and was added in an amount of about 100 ng onto the membrane, followed by hybridization at 65° C. for 18 hrs. The membrane was washed twice with 2×SSC/1% SDS at room temperature for 5 min, then twice with 0.1×SSC/1% SDS at room temperature for 15 min, and finally twice with 1×SSC at room temperature for 5 min. Probe detection was performed using a Southern-star™ kit (Tropix, USA). The blots were treated with a blocking buffer (1×PBS, 0.2% I-Block™ Reagent and 0.5% SDS) and labeled with alkaline phosphatase-conjugated streptavidin, followed by treatment with CDP-Star™ (Ready-to-Use). The membrane was exposed to an X-ray film (Fujifilm, Japan) for a period ranging from 10 min to 1.5 hrs.

2. Expression pattern of IbExpansin

An about 1 kb IbExpansin EST clone of sweetpotato was labeled with biotin in PCR and was used in Northern blotting as probe.

Figure 7:
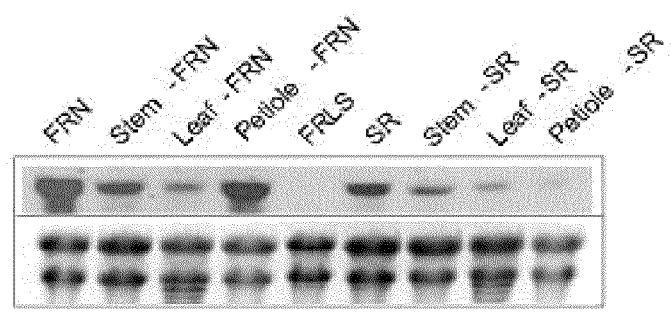
FIG. 7 presents the results of Northern Blot Analysis showing the expression patterns of sweetpotato expansin gene in sweetpotato.

Expression of IbExpansin was detected in the tissues in a non-storage root stage, including FRN, Stem-FRN, Leaf-FRN and Petiole-FRN, with the highest level in FRN and Petiole-FRN. However, a remarkably decreased level of expression of IbExpansin was detected in the tuberous tissue in a late storage root stage, along with significantly low levels in stems and leaves at storage root-stage (FIG. 7). These expression patterns strongly imply that IbExpansin is related to the elongation growth of roots in the early stage of storage root development, and that its activity does not promote the development of storage root.

EXAMPLE 4

Construction of Binary Vector

Figure 8:
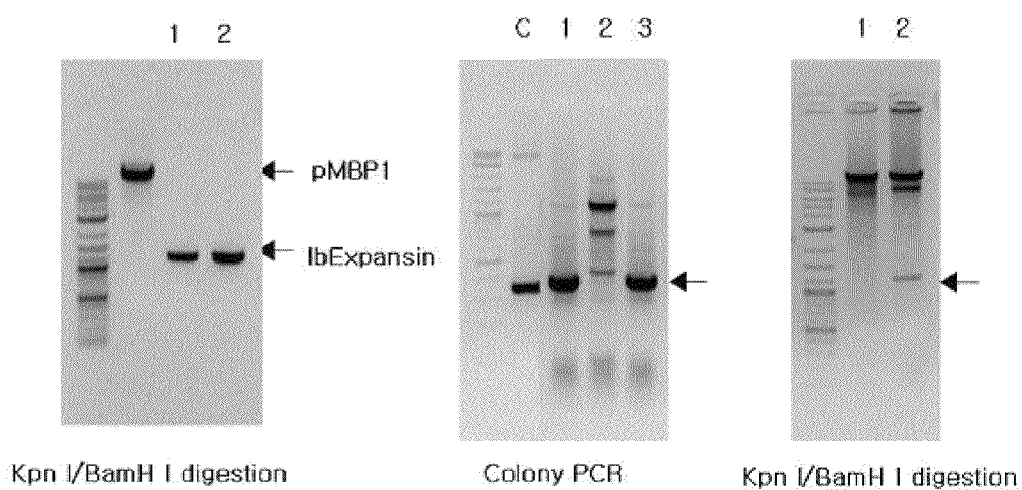
FIG. 8 shows results obtained at various process stages of constructing a binary vector for carrying the antisense DNA of sweetpotato expansin cDNA of the present invention into sweetpotatoes.

A 5' primer (SEQ ID NO.: 10) was synthesized with KpnI restriction site and a 3' primer was synthesized with BamHI restriction site to construct a knock-out binary vector. PCR was performed with the primers to obtain a full-length IbExpansin (NCBI accession number: DQ515800) cDNA. The PCR product was inserted into a pGEM-T Easy vector, and digested the pGEM-T Easy vector with BamHI and KpnI to excise the cDNA therefrom. The cDNA digest was inserted in the antisense direction between a CaMV35S promoter and an NOS terminator in a pMBP1 vector to construct the binary vector pIbExpansin-anti (FIG. 9). The insertion was confirmed by colony PCR and restriction enzyme digestion (FIG. 8)

EXAMPLE 5

Induction of Embryogenic Callus in Sweetpotato

The stem of the sweetpotato, named 'Youlmi' was cut to be with an axillary bud and cultured on MS basal medium (Murashige and Skoog, 1962) under a cool-white fluorescent lamp with 1,000 lux and a photoperiod condition of 16 hours for the in vitro culturing of sweetpotato. An apical meristem having a height of about 150 um and a diameter of about 350 um was removed from the cultured stem after removing young leaves under a dissecting microscope, and the medium was contacted with the cut surface of the apical meristem (Cantliffe et al., 1987; Liu et al., 1989). For induction of the embryogenic callus, MS basal medium was prepared by adding 100 mg/L myo-inositol, 0.4 mg/L thiamine-HCl, 30 g/L sucrose, and 4 g/L Gelrite to MS inorganic salt, adjusted to pH 5.8, added 1 mg/L 2,4-D, and used in the Petri dish (Resulting medium was referred as MS1D).

This callus was subcultured on the same medium a one month intervals (FIG. 10).

EXAMPLE 6

Transformation of Sweetpotato Using the Gene Gun and Screening of the Sweetpotato Transformant The embryogenic callus was cut into cell clusters 1-2 mm in diameter. About 50-60 callus clusters were put in the center part of a Petri dish containing MS1D medium, cultured for one day, and then bombarded. Particle bombardment was carried out under vacuum condition with 1,100 PSi using helium gas. The bombardment was carried out according to the method of Sanford et al., which involves bombardment with gold particles coated with DNA at intervals of 6 cm from the callus clusters, using 1.0 μg DNA and helium gas with 1,100 PSi pressure. After culturing in the dark at a temperature of 25° C. for 2 days, the bombardment was carried out once more under the same conditions. After culturing in the dark at a temperature of 25° C. for one week, the callus clusters were subcultured on MS1D solidified medium containing 100 mg/L kanamycin (selection medium) at a temperature of 25° C. and about 2,000 lux for 2 months. To facilitate the recovery of the callus stressed on the selection medium and the differentiation of shoots, the selected callus clusters were transferred to MS1D solidified medium containing 10 mg/L 2iP and 100 mg/L kanamycin. One month after transfer to the selection medium, the callus with a light green color was preferentially transferred to MS basal medium to induce a young bud, and transferred to the medium containing 20 mg/L NAA to induce root development. Subculture was carried out approximately once every two weeks.

The callus, beginning to develop buds and roots, was regenerated into a plant on the MS basal medium. DNA was isolated from the leaves of the transformed plant with the aid of QIAquick™ plant DNA miniprep kit (QIAGEN, Germany).

Figure 11:
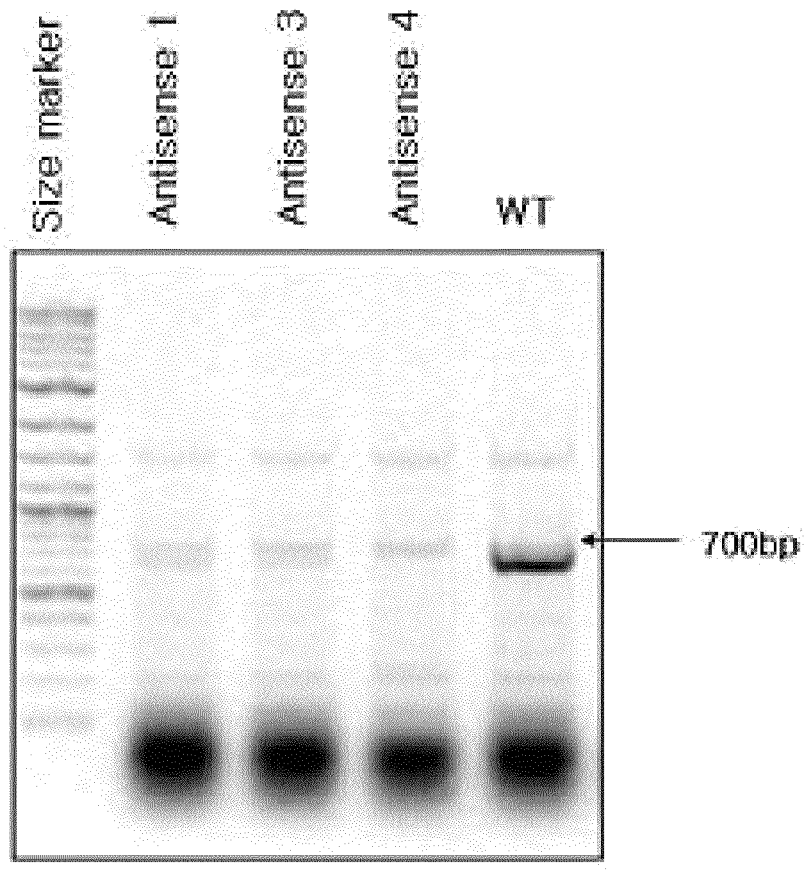
FIG. 11 is a view showing the result of electrophoresis to examine the insertion of antisense DNA of IbExpansin cDNA in sweetpotato transformant expressing the antisense DNA of sweetpotato expansin cDNA of the present invention.

PCR was performed using the isolated DNA, using primer NPT II 5' (GAGGCTATTCGGCTATGACTG-SEQ ID NO.: 12), and primer NPT II 3' (ATCGGGAGCGGCGATAC-CGTA-SEQ ID NO.: 13) together, starting from pre-denaturation at 95° C. for 5 min, with 30 cycles of denaturation at 95° C. for 30 sec, annealing at 65° C. for 30 sec and extension at 72° C. for 1 min. The PCR products thus produced were separated by 1% agarose gel electrophoresis to detect a 700 bp band (FIG. 11).

EXAMPLE 7

Expression Analysis of Transgenic Sweetpotato

Figure 12:
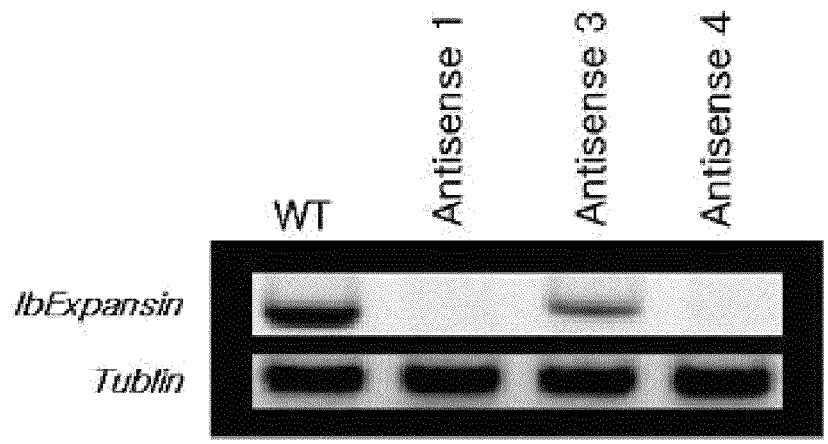
FIG. 12 is a view showing the result of electrophoresis to examine the expression of IbExpansin in sweetpotato transformant expressing the antisense DNA of sweetpotato expansin cDNA of the present invention.

RNA was isolated from leaves of the transformed sweetpotato with the aid of 4.4 M guanidinium-SDS lysis buffer (chirgwin et al., 1979), and 5.7M CsCl gradient method (Glisin et al., 1974). The total amount of sample containing total RNA 6 μg, and dNTP Oligo dT primer 10 pmole was adjusted to 13 ul, denatured at 68° C. for 5 min, and then immediately transferred to ice. After adding 5×RT-buffer 4 μl, RNase inhibitor (RNasin) 1 μl, 0.1 M DTT 1 μl, and 200 U/μl of reverse transcriptase (Superscript III) to each sample, reverse-transcription was performed at 50° C. for 80 min, and was then denatured immediately at 70° C. for 15 min. 30 μl of distilled water was added to each sample. RT-PCR was performed using the obtained cDNA as a template. PCR was performed using IbExpansin gene specific primers (5' TTC CAGATA AGG TGT GTG AAC 3'; SEQ ID NO.: 14, 5' ACT GTC TCC ACA CTC AGC 3'; SEQ ID NO.: 15), starting from pre-denaturation at 95° C. for 5 min, with 30 cycles of denaturation at 95° C. for 30 sec, annealing at 58° C. for 30 sec and extension at 72° C. for 1 min. To construct an internal equal loading control, PCR was performed using primer tublin-1 (5'CAA CTA CCA GCC ACC AAC TGT 3'; SEQ ID NO.: 16) and primer tublin-2(5'CAA GAT CCT CAC GAG CTT CAC 3'; SEQ ID NO.: 17) under the same conditions as the IbExpansin. The PCR products thus produced were separated by 1% agarose gel electrophoresis. It was found that antisense line No. 1 and No. 4 were perfect knock-outs and that antisense line No. 3 was a knock-down, decreasing the expression level (FIG. 12).

EXAMPLE 8

Analysis of Transgenic Sweetpotato Root Development

Figure 13:
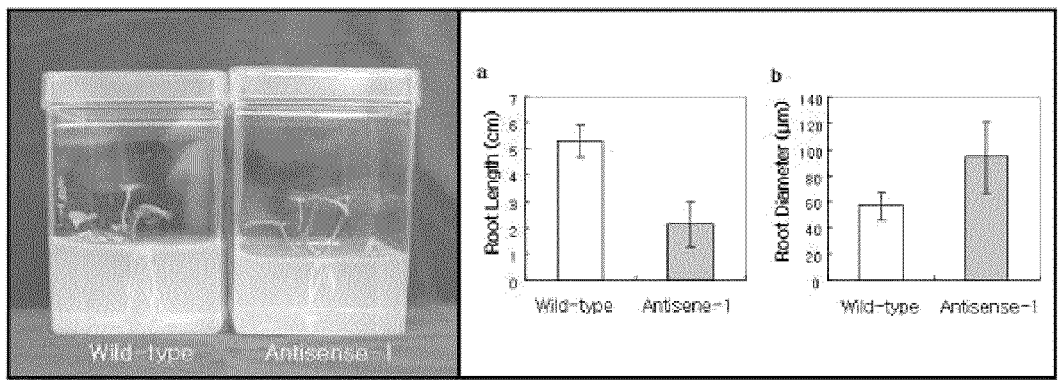
FIG. 13 shows the comparison of root growth between sweetpotato transformant expressing the antisense DNA of sweetpotato expansin cDNA of the present invention and wild-type at 10 days after cutting in vitro.
Figure 14:
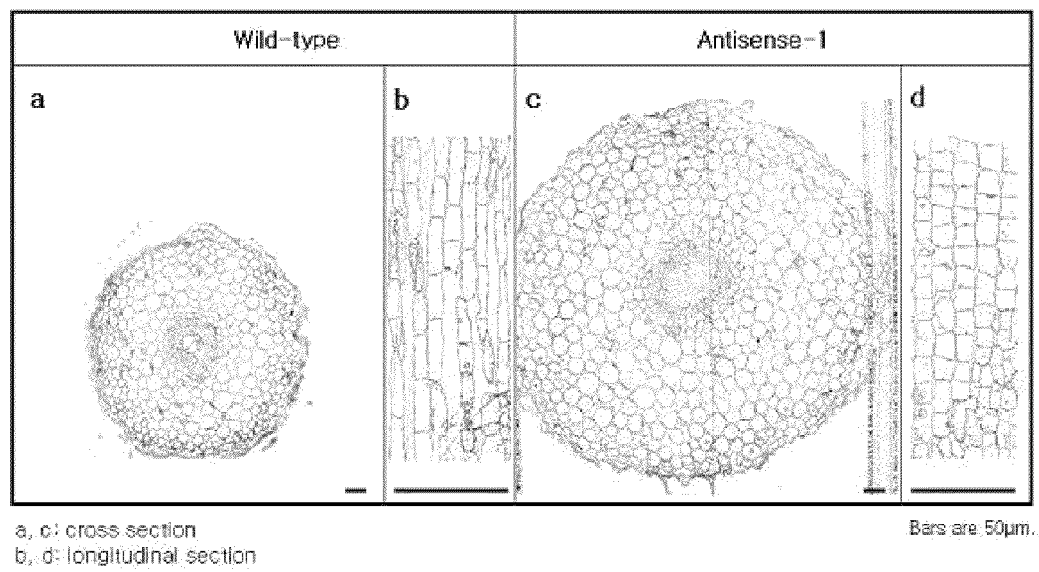
FIG. 14 shows the comparison of root growth on a cellular level between sweetpotato transformant expressing the antisense DNA of sweetpotato expansin cDNA of the present invention and wild-type at 10 days after cutting in vitro, wherein (a) and (c) of FIG. 14 show the cross-section, and (b) and (d) of FIG. 14 show longitudinal section.

Cuttings of the IbExpansin-antisense No. 1 sweetpotato and wild-type were conducted in MS basal medium on the same date. 10 days after the cutting, development patterns of roots were compared between transgenic sweetpotato No. 1 and wild-type (FIGS. 13 and 14). The fibrous roots were observed with the naked eye. It was found that the fibrous roots of the transgenic sweetpotato No. 1 was shorter (2-3 cm) in length and 2-3 times bigger in diameter than those of the wild-type with thin diameter and 5-6 cm length (FIG. 13).

The maturation zone of the root was cut, fixed at 4° C. for 10 days in 25 mM potassium phosphate buffer (pH 7.0) including 2% Paraformaldehyde and 2.5% Glutaraldehyde, washed with buffer twice, 50, 60, 70, 80, 90, 95, and 100% ethanol were changed serially to remove moisture, and then put in the capsule holding resin which had solidified one day earlier, after serially replacing the mixtures having ratios of resin to ethanol of 1:3, 1:1, 3:1 and 1:0, and solidified at 58° C. after adding the undiluted resin on the solidified resin in the capsule once more.

After the resin hardened, the sample was cut widthwise and lengthwise respectively, and the shape of root cells was observed under a microscope. It was found that cells of the wild type were thin and long compared with the transformant, and on the contrary, cells of the transformant were short and thick compared with the wild-type (FIG. 14). In addition, in the case of transformant, it was observed that cell differentiation occurred actively within the primary cambium, so that cell differentiation was begun within the second cambium to develop storage root. Therefore, expression of the antisense DNA of IbExpansin cDNA according to the present invention can advance the onset of the storage root development.

EXAMPLE 9

Analysis of Transgenic Sweetpotato Storage Root Development

Figures 15, 16:
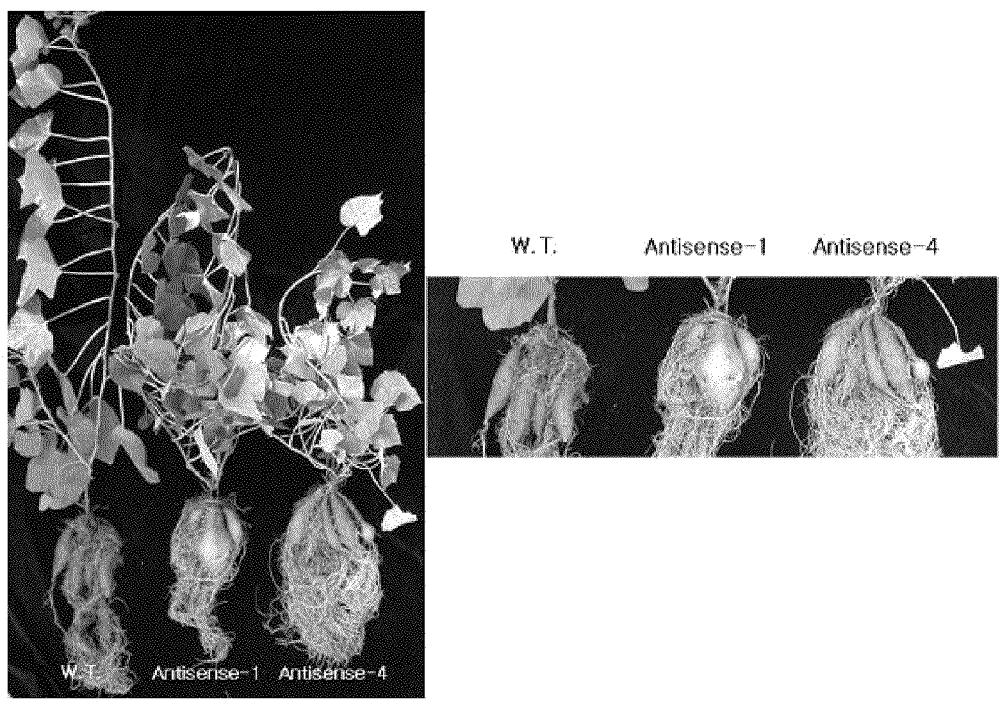
FIG. 15 shows the comparison of growth between sweetpotato transformant expressing the antisense DNA of sweetpotato expansin cDNA of the present invention and wild-type.
FIG. 16 shows the comparison of storage root production between sweetpotato transformant expressing the antisense DNA of sweetpotato expansin cDNA of the present invention and wild-type.

Cuttings of the transgenic sweetpotato No. 1, No. 4, and wild-type were conducted on the same day. 5 months after the cutting, development patterns of their aerial parts and storage roots and production were compared with one another (FIGS. 15 and 16). As for the growth of the aerial part, the wild type had a fewer number of branches and its first branch was very long. On the other hand, it was found that the transgenic sweetpotato had more branches but that the length of its branches was about the same, and that the first branch were much shorter than the first branch of the wild type. Total aerial part biomass showed no difference between the transgenic sweetpotato and the wild type. There was a great difference between the transformant and the wild type in the development of storage root. In the wild type a part of its primary roots developed into storage roots, but in the transformant most of its primary roots developed into storage roots, so that transformant was superior to the wild-type in total storage root number by up to two times, and in total biomass by up to one and half times. There was a difference in the position from which storage root develop, namely, the primary roots of the wide type grew to about 5-10 cm in length and then developed into storage roots, but the primary roots of the transformant developed into storage roots at the beginning point of the primary roots' development.

Therefore, the antisense DNA of IbExpansin cDNA according to the present invention can be applied to the generation of highly productive transgenic sweetpotato to increase the storage root production usefully.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The invention claimed is:

1. A method for increasing storage root production of sweetpotato, comprising:
   introducing an antisense DNA of IbExpansin cDNA into the sweetpotato, wherein the antisense DNA comprises the nucleotide sequence of SEQ ID NO.: 9, and wherein the sweet potato into which the antisense DNA is introduced produces an increased amount of storage root compared to a wild-type sweetpotato.

2. The method of claim 1, wherein the antisense DNA of IbExpansin cDNA is introduced into the sweetpotato by introducing a binary vector containing the antisense DNA into a sweetpotato.

3. A method for preparing a transgenic sweetpotato with a capacity of increased storage root production, comprising:
   introducing an antisense DNA of IbExpansin cDNA into a sweetpotato to produce the transgenic sweetpotato plant, wherein the antisense DNA comprises the nucleotide sequence of SEQ ID NO.: 9.

4. The method of claim 1, wherein the antisense DNA is amplified by PCR with a pair of PCR primers, the pair of PCR primers being the nucleotides of SEQ ID NO.: 10 and 11, respectively.

* * * * *

SEQUENCE LISTING

```
<160> NUMBER OF SEQ ID NOS: 23

<210> SEQ ID NO 1
<211> LENGTH: 1213
<212> TYPE: DNA
<213> ORGANISM: Ipomoea batatas

<400> SEQUENCE: 1
cattcctcta ccaattcaac tgaagcaata acaatggcgg ttcttgagct tcttctggtc      60
ggagttcttg ccacgttgtc tccggtgcat ggctactggg gctggagcag cgctcgcgcc     120
accttctacg gcggcggtga tgcttctgga acaatgggcg gagcctgcgg gtatgggaac     180
ctgtatagct caggctatgg caccaacact gcggcactta gcaccgctct gttcaacaat     240
gggctcagct gcgggtcctg tttccagata aggtgtgtga acgaccggtc ctgcctccgc     300
ggcgtaatca ccgtcaccgc caccaatttc tgcccgcccg gcggctggtg cgagcccccc     360
aacccacact ttgatctctc tcagcctgtt ttcttgagaa ttgcccagta cagagccgga     420
gttgttcccg ttgcttaccg acgggtgcct tgcaggagga gtggaggaat caggttcacc     480
attaacggcc atgctttctt caacctggta ctagtaacca acgtgggagg ctccggcgac     540
gtacacgccg tgtacatcaa aggatcaaga accgggtggc aaatgatgtc cagaaactgg     600
ggccaaaact ggcagagcaa cgccaacctc aacggccaaa gcctctcatt ccgggtggtc     660
accggcgaca gccgcagcgt cgtctcctac aacgccgctc ccccggctg gtccttcggc      720 cagacctact ccggcgccca gttccgctag gccggaattc atcaaacacc cccattttt     780 tcccgccata tatatgat ctccaaacct atacataact aaagcctaca ccatttttac       840
aagtttgaaa tgcaattaaa gtcatgggga tgggaaaatg ttgatcaagt ttccggccgc     900
cctctctcac ttttttttct aaaagggatt ggttttgatc gaaagcccct ttggccatga     960
aaattggcca ttcaatcaac aagaattgaa gcagagttga agtggtagtt agttatatca    1020
agattgtgct accccatgac tagcttaatt agtactgcat tatttatgtg attattatta    1080
ttatgcagac aaaatgtgtc tgcataccta ccctgtggaa caacattaat ttttttttcc    1140
tcgtcttctt cgtcgtcgtt tgtaattagt atagcattaa ggttaaacag ctaatgctga    1200
```
gtgtggagac agt                                                          1213

<210> SEQ ID NO 2
<211> LENGTH: 238
<212> TYPE: PRT
<213> ORGANISM: Ipomoea batatas

<400> SEQUENCE: 2

Met Ala Val Leu Glu Leu Leu Val Gly Val Leu Ala Thr Leu
 1               5                  10                  15

Ser Pro Val His Gly Tyr Trp Gly Trp Ser Ser Ala Arg Ala Thr
                20                  25                  30

Phe Tyr Gly Gly Gly Asp Ala Ser Gly Thr Met Gly Gly Ala Cys
                35                  40                  45

Gly Tyr Gly Asn Leu Tyr Ser Ser Gly Tyr Gly Thr Asn Thr Ala
                50                  55                  60

Ala Leu Ser Thr Ala Leu Phe Asn Asn Gly Leu Ser Cys Gly Ser
                65                  70                  75

Cys Phe Gln Ile Arg Cys Val Asn Asp Arg Ser Cys Leu Arg Gly
                80                  85                  90

Val Ile Thr Val Thr Ala Thr Asn Phe Cys Pro Pro Gly Gly Trp
                95                 100                 105

Cys Glu Pro Pro Asn Pro His Phe Asp Leu Ser Gln Pro Val Phe
               110                 115                 120

Leu Arg Ile Ala Gln Tyr Arg Ala Gly Val Val Pro Val Ala Tyr
               125                 130                 135

Arg Arg Val Pro Cys Arg Arg Ser Gly Ile Arg Phe Thr Ile
               140                 145                 150

Asn Gly His Ala Phe Phe Asn Leu Val Leu Val Thr Asn Val Gly
               155                 160                 165

Gly Ser Gly Asp Val His Ala Val Tyr Ile Lys Gly Ser Arg Thr
               170                 175                 180

Gly Trp Gln Met Met Ser Arg Asn Trp Gly Gln Asn Trp Gln Ser
               185                 190                 195

Asn Ala Asn Leu Asn Gly Gln Ser Leu Ser Phe Arg Val Val Thr
               200                 205                 210

Gly Asp Ser Arg Ser Val Val Ser Tyr Asn Ala Ala Pro Pro Gly
               215                 220                 225

Trp Ser Phe Gly Gln Thr Tyr Ser Gly Ala Gln Phe Arg
               230                 235

<210> SEQ ID NO 3
<211> LENGTH: 28
<212> TYPE: DNA
<213> ORGANISM: Artificial
<220> FEATURE:
<223> OTHER INFORMATION: Synthetic construct

<400> SEQUENCE: 3
gggcagaaat tggtggcggg tgacggtg                                          28

<210> SEQ ID NO 4
<211> LENGTH: 28
<212> TYPE: DNA
<213> ORGANISM: Artificial
<220> FEATURE:
<223> OTHER INFORMATION: Synthetic construct

<400> SEQUENCE: 4

```
acaggacccg cagctgaccc cattgttg                                          28

<210> SEQ ID NO 5
<211> LENGTH: 33
<212> TYPE: DNA
<213> ORGANISM: Artificial
<220> FEATURE:
<223> OTHER INFORMATION: Synthetic construct

<400> SEQUENCE: 5
gtaggatccc attcctctac caattcaact gaa                                    33

<210> SEQ ID NO 6
<211> LENGTH: 30
<212> TYPE: DNA
<213> ORGANISM: Artificial
<220> FEATURE:
<223> OTHER INFORMATION: Synthetic construct

<400> SEQUENCE: 6
gatggtacca ctgtctccac actcagcatt                                        30

<210> SEQ ID NO 7
<211> LENGTH: 20
<212> TYPE: DNA
<213> ORGANISM: Artificial
<220> FEATURE:
<223> OTHER INFORMATION: Synthetic construct

<400> SEQUENCE: 7
aattaaccct cactaaaggg                                                   20

<210> SEQ ID NO 8
<211> LENGTH: 22
<212> TYPE: DNA
<213> ORGANISM: Artificial
<220> FEATURE:
<223> OTHER INFORMATION: Synthetic construct

<400> SEQUENCE: 8
cgggatatca ctcagcataa tg                                                22

<210> SEQ ID NO 9
<211> LENGTH: 1213
<212> TYPE: DNA
<213> ORGANISM: Ipomoea batatas

<400> SEQUENCE: 9
actgtctcca cactcagcat tagctgttta accttaatgc tatactaatt acaaacgacg       60
acgaagaaga cgaggaaaaa aaaattaatg ttgttccaca gggtaggtat gcagacacat      120
tttgtctgca taataataat aatcacataa ataatgcagt actaattaag ctagtcatgg      180
ggtagcacaa tcttgatata actaactacc acttcaactc tgcttcaatt cttgttgatt      240
gaatggccaa ttttcatggc caaaagggct ttcgatcaaa accaatccct tttagaaaaa      300
aaagtgagag agggcggccg gaaacttgat caacattttc ccatccccat gactttaatt      360
gcatttcaaa cttgtaaaaa tggtgtaggc tttagttatg tataggtttg gagatcatat      420
atatatggcg ggaaaaaaat gggggtgttt gatgaattcc ggcctagcgg aactgggcgc      480
cggagtaggt ctggccgaag gaccagccgg ggggagcggc gttgtaggag acgacgctgc      540
ggctgtcgcc ggtgaccacc cggaatgaga ggctttggcc gttgaggttg gcgttgctct      600
gccagttttg gccccagttt ctggacatca tttgccaccc ggttcttgat cctttgatgt      660
```

```
acacggcgtg tacgtcgccg gagcctccca cgttggttac tagtaccagg ttgaagaaag    720
catggccgtt aatggtgaac ctgattcctc cactcctcct gcaaggcacc cgtcggtaag    780
caacgggaac aactccggct ctgtactggg caattctcaa gaaaacaggc tgagagagat    840
caaagtgtgg gttggggggc tcgcaccagc cgccgggcgg gcagaaattg gtggcggtga    900
cggtgattac gccgcggagg caggaccggt cgttcacaca ccttatctgg aaacaggacc    960
cgcagctgag cccattgttg aacagagcgg tgctaagtgc cgcagtgttg gtgccatagc   1020
ctgagctata caggttccca tacccgcagg ctccgcccat tgttccagaa gcatcaccgc   1080
cgccgtagaa ggtggcgcga gcgctgctcc agcccagta  gccatgcacc ggagacaacg   1140
tggcaagaac tccgaccaga agaagctcaa gaaccgccat tgttattgct tcagttgaat   1200
tggtagagga atg                                                      1213
```

```
<210> SEQ ID NO 10
<211> LENGTH: 33
<212> TYPE: DNA
<213> ORGANISM: Artificial
<220> FEATURE:
<223> OTHER INFORMATION: Synthetic construction

<400> SEQUENCE: 10
gatggtaccc attcctctac caattcaact gaa                                 33

<210> SEQ ID NO 11
<211> LENGTH: 30
<212> TYPE: DNA
<213> ORGANISM: Artificial
<220> FEATURE:
<223> OTHER INFORMATION: Synthetic construct

<400> SEQUENCE: 11
gatggatcca ctgtctccac actcagcatt                                     30

<210> SEQ ID NO 12
<211> LENGTH: 21
<212> TYPE: DNA
<213> ORGANISM: Artificial
<220> FEATURE:
<223> OTHER INFORMATION: Synthetic construct

<400> SEQUENCE: 12
gaggctattc ggctatgact g                                              21

<210> SEQ ID NO 13
<211> LENGTH: 21
<212> TYPE: DNA
<213> ORGANISM: Artificial
<220> FEATURE:
<223> OTHER INFORMATION: Synthetic construct

<400> SEQUENCE: 13
atcgggagcg gcgataccgt a                                              21

<210> SEQ ID NO 14
<211> LENGTH: 21
<212> TYPE: DNA
<213> ORGANISM: Artificial
<220> FEATURE:
<223> OTHER INFORMATION: Synthetic construct

<400> SEQUENCE: 14
ttccagataa ggtgtgtgaa c                                              21
```

```
<210> SEQ ID NO 15
<211> LENGTH: 18
<212> TYPE: DNA
<213> ORGANISM: Artificial
<220> FEATURE:
<223> OTHER INFORMATION: Synthetic construct

<400> SEQUENCE: 15
actgtctcca cactcagc                                                     18

<210> SEQ ID NO 16
<211> LENGTH: 21
<212> TYPE: DNA
<213> ORGANISM: Artificial
<220> FEATURE:
<223> OTHER INFORMATION: Synthetic construct

<400> SEQUENCE: 16
caactaccag ccaccaactg t                                                 21

<210> SEQ ID NO 17
<211> LENGTH: 21
<212> TYPE: DNA
<213> ORGANISM: Artificial
<220> FEATURE:
<223> OTHER INFORMATION: Synthetic construct

<400> SEQUENCE: 17
caagatcctc acgagcttca c                                                 21

<210> SEQ ID NO 18
<211> LENGTH: 252
<212> TYPE: PRT
<213> ORGANISM: Prunus cerasus

<400> SEQUENCE: 18
```

Met Lys Met Ala Leu Ala Tyr Gly Phe Cys Leu Val Gly Leu Leu Ala
 1               5                  10                  15

Met Val Ser Cys Ala His Ala Tyr Gly Gly Gly Gly Trp Val Asn Ala
            20                  25                  30

Arg Ala Thr Phe Tyr Gly Gly Gly Asp Ala Ser Gly Thr Met Gly Gly
        35                  40                  45

Ala Cys Gly Tyr Gly Asn Leu Tyr Ser Gln Gly Tyr Gly Thr Asn Thr
    50                  55                  60

Ala Ala Leu Ser Thr Ala Leu Phe Asn Asn Gly Leu Gly Cys Gly Ser
65                  70                  75                  80

Cys Tyr Glu Ile Arg Cys Val Asn Asp Pro Lys Trp Cys Leu Pro Gly
                85                  90                  95

Ala Ile Val Val Thr Ala Thr Asn Phe Cys Pro Pro Asn Asn Ala Leu
            100                 105                 110

Pro Asn Asn Ala Gly Gly Trp Cys Asn Pro Pro Gln His His Phe Asp
        115                 120                 125

Leu Ser Gln Pro Val Phe Gln His Ile Ala Gln Tyr Lys Ala Gly Val
    130                 135                 140

Val Pro Val Ala Tyr Arg Arg Val Pro Cys Arg Arg Gly Gly Ile
145                 150                 155                 160

Arg Phe Thr Ile Asn Gly His Ser Tyr Phe Asn Leu Val Leu Ile Thr
                165                 170                 175

Asn Val Gly Gly Ala Gly Asp Val His Ser Val Ser Val Lys Gly Ser
            180                 185                 190

```
Arg Thr Gly Trp Gln Ala Met Ser Arg Asn Trp Gly Gln Asn Trp Gln
            195                 200                 205

Ser Asn Ser Tyr Leu Asn Gly Gln Ser Leu Ser Phe Lys Val Thr Thr
            210                 215                 220

Ser Asp Gly Arg Thr Val Val Ala Tyr Asn Ala Ala Pro Ala Gly Trp
225                 230                 235                 240

Ser Phe Gly Gln Thr Tyr Ser Gly Ala Gln Phe Arg
            245                 250

<210> SEQ ID NO 19
<211> LENGTH: 252
<212> TYPE: PRT
<213> ORGANISM: Prunus persica

<400> SEQUENCE: 19

Met Lys Met Ala Leu Ala Tyr Gly Phe Cys Leu Val Gly Leu Leu Ala
1               5                   10                  15

Met Val Ser Cys Ala His Ala Tyr Gly Gly Gly Gly Trp Val Asn Ala
            20                  25                  30

Arg Ala Thr Phe Tyr Gly Gly Gly Asp Ala Ser Gly Thr Met Gly Gly
        35                  40                  45

Ala Cys Gly Tyr Gly Asn Leu Tyr Ser Gln Gly Tyr Gly Thr Asn Thr
    50                  55                  60

Ala Ala Leu Ser Thr Ala Leu Phe Asn Asn Gly Leu Gly Cys Gly Ser
65                  70                  75                  80

Cys Tyr Glu Ile Arg Cys Val Ser Asp Pro Lys Trp Cys Leu Pro Gly
                85                  90                  95

Ala Ile Val Val Thr Ala Thr Asn Phe Cys Pro Pro Asn Asn Ala Leu
            100                 105                 110

Pro Asn Asn Ala Gly Gly Trp Cys Asn Pro Pro Gln His His Phe Asp
        115                 120                 125

Leu Ser Gln Pro Val Phe Gln His Ile Ala Gln Tyr Lys Ala Gly Val
    130                 135                 140

Val Pro Val Ala Tyr Arg Arg Val Pro Cys Arg Arg Arg Gly Gly Ile
145                 150                 155                 160

Arg Phe Thr Ile Asn Gly His Ser Tyr Phe Asn Leu Val Leu Ile Thr
                165                 170                 175

Asn Val Gly Gly Ala Gly Asp Val His Ser Val Ser Val Lys Gly Ser
            180                 185                 190

Arg Thr Gly Trp Gln Ala Met Ser Arg Asn Trp Gly Gln Asn Trp Gln
        195                 200                 205

Ser Asn Ser Tyr Leu Asn Gly Gln Ser Leu Ser Phe Lys Val Thr Thr
    210                 215                 220

Ser Asp Gly Arg Thr Val Val Ser Tyr Asn Ala Ala Pro Ala Gly Trp
225                 230                 235                 240

Ser Phe Gly Gln Thr Tyr Ser Gly Ala Gln Phe Arg
                245                 250

<210> SEQ ID NO 20
<211> LENGTH: 252
<212> TYPE: PRT
<213> ORGANISM: Prunus avium

<400> SEQUENCE: 20

Met Lys Met Ala Leu Ala Tyr Gly Phe Cys Leu Val Gly Leu Leu Ala
1               5                   10                  15

Met Val Ser Cys Ala His Ala Tyr Gly Gly Gly Gly Trp Val Asp Ala
```

-continued

```
                 20                  25                  30
Arg Ala Thr Phe Tyr Gly Gly Ser Asp Ala Ser Gly Thr Met Gly Gly
             35                  40                  45
Ala Cys Gly Tyr Gly Asn Leu Tyr Ser Gln Gly Tyr Gly Thr Asn Thr
 50                  55                  60
Ala Ala Leu Ser Thr Ala Leu Phe Asn Asn Gly Leu Gly Cys Gly Ser
 65                  70                  75                  80
Cys Tyr Glu Ile Arg Cys Val Asn Asp Pro Lys Trp Cys Leu Pro Gly
                 85                  90                  95
Ala Ile Val Val Thr Ala Thr Asn Phe Cys Pro Pro Asn Asn Ala Leu
            100                 105                 110
Pro Asn Asn Ala Gly Gly Trp Cys Asn Pro Pro Gln His His Phe Asp
            115                 120                 125
Leu Ser Gln Pro Val Phe Gln His Ile Ala Gln Tyr Lys Ala Gly Val
            130                 135                 140
Val Pro Val Ala Tyr Arg Arg Val Pro Cys Arg Arg Gly Gly Ile
145                 150                 155                 160
Arg Phe Thr Ile Asn Gly His Ser Tyr Phe Asn Leu Val Leu Ile Thr
                165                 170                 175
Asn Val Gly Gly Ala Gly Asp Val His Ser Val Ser Val Lys Gly Ser
            180                 185                 190
Arg Thr Gly Trp Gln Ala Met Ser Arg Asn Trp Gly Gln Asn Trp Gln
            195                 200                 205
Ser Asn Ser Tyr Leu Asn Gly Gln Ser Leu Ser Phe Lys Val Thr Thr
            210                 215                 220
Ser Asp Gly Arg Thr Val Val Ser Tyr Asn Ala Ala Pro Ala Gly Trp
225                 230                 235                 240
Ser Phe Gly Gln Thr Tyr Ser Gly Ala Gln Leu Arg
                245                 250
```

<210> SEQ ID NO 21
<211> LENGTH: 239
<212> TYPE: PRT
<213> ORGANISM: Capsicum annuum

<400> SEQUENCE: 21

```
Met Ala Leu Leu Gly Leu Leu Met Gly Ile Ser Leu Met Phe Gln
 1               5                  10                  15
Ser Val His Gly Tyr Gly Gly Trp Ile Asn Ala His Ala Thr Phe Tyr
             20                  25                  30
Gly Gly Gly Asp Ala Ser Gly Thr Met Gly Gly Ala Cys Gly Tyr Gly
             35                  40                  45
Asn Leu Tyr Ser Ser Gly Tyr Gly Thr Asn Thr Ala Ala Leu Ser Thr
 50                  55                  60
Ala Leu Phe Asn Asn Gly Leu Ser Cys Gly Gln Cys Phe Gln Leu Met
 65                  70                  75                  80
Cys Val Asn Ala Arg Gln Tyr Cys Leu Pro Gly Ile Ile Thr Val Thr
                 85                  90                  95
Ala Thr Asn Phe Cys Pro Pro Gly Gly Trp Cys Asp Pro Pro Asn His
            100                 105                 110
His Phe Asp Leu Ser Gln Pro Ile Phe Leu Arg Ile Ala Gln Tyr Arg
            115                 120                 125
Ala Gly Ile Val Pro Val Ala Tyr Arg Arg Val Pro Cys Arg Arg Arg
            130                 135                 140
Gly Gly Ile Arg Phe Thr Ile Asn Gly His Ser Tyr Phe Asn Leu Val
```

```
145                 150                 155                 160
Leu Val Thr Asn Val Gly Gly Ser Gly Asp Val His Ser Val Tyr Ile
                165                 170                 175

Lys Gly Ser Arg Thr Gln Trp Gln Pro Met Ser Arg Asn Trp Gly Gln
            180                 185                 190

Asn Trp Gln Asn Asn Ala Tyr Leu Asn Gly Gln Ser Leu Ser Phe Lys
        195                 200                 205

Val Thr Thr Gly Asp Gly Arg Thr Val Val Ser Tyr Asn Ala Ala Pro
    210                 215                 220

Ser Ser Trp Ser Phe Gly Gln Thr Phe Ser Gly Gly Gln Phe Arg
225                 230                 235

<210> SEQ ID NO 22
<211> LENGTH: 239
<212> TYPE: PRT
<213> ORGANISM: Lycopersicon esculentum

<400> SEQUENCE: 22

Met Ala Leu Leu Ala Ile Leu Leu Met Gly Ile Ser Leu Met Phe Gln
1               5                   10                  15

Ser Ala His Gly Tyr Gly Gly Trp Ile Asn Ala His Ala Thr Phe Tyr
                20                  25                  30

Gly Gly Gly Asp Ala Ser Gly Thr Met Gly Gly Ala Cys Gly Tyr Gly
            35                  40                  45

Asn Leu Tyr Ser Thr Gly Tyr Gly Thr Asn Thr Ala Ala Leu Ser Thr
        50                  55                  60

Ala Leu Phe Asn Asn Gly Leu Ser Cys Gly Ala Cys Phe Gln Leu Met
65                  70                  75                  80

Cys Val Asn Ala Gly Gln Tyr Cys Leu Pro Gly Ile Ile Thr Val Thr
                85                  90                  95

Ala Thr Asn Phe Cys Pro Pro Gly Gly Trp Cys Asp Pro Pro Arg Pro
            100                 105                 110

His Phe Asp Leu Ser Gln Pro Ile Phe Leu Arg Ile Ala Gln Tyr Arg
        115                 120                 125

Ala Gly Ile Val Pro Val Ala Tyr Arg Arg Val Pro Cys Arg Arg Ser
    130                 135                 140

Gly Gly Ile Arg Phe Thr Ile Asn Gly His Ser Tyr Phe Asn Leu Val
145                 150                 155                 160

Leu Val Thr Asn Val Gly Gly Ser Gly Asp Val His Ser Val Tyr Ile
                165                 170                 175

Lys Gly Ser Arg Thr Gln Trp Gln Pro Met Ser Arg Asn Trp Gly Gln
            180                 185                 190

Asn Trp Gln Asn Asn Ala Tyr Leu Asn Gly Gln Ser Leu Ser Phe Lys
        195                 200                 205

Val Thr Thr Gly Asp Gly Arg Thr Val Val Ser Tyr Asn Ala Ala Pro
    210                 215                 220

Ser Ser Trp Ser Phe Gly Gln Thr Phe Ser Gly Gly Gln Phe Arg
225                 230                 235

<210> SEQ ID NO 23
<211> LENGTH: 249
<212> TYPE: PRT
<213> ORGANISM: Ipomoea batatas

<400> SEQUENCE: 23

His Ser Ser Thr Asn Ser Thr Glu Ala Ile Thr Met Ala Val Leu Glu
1               5                   10                  15
```

-continued

```
Leu Leu Leu Val Gly Val Leu Ala Thr Leu Ser Pro Val His Gly Tyr
            20                  25                  30

Trp Gly Trp Ser Ser Ala Arg Ala Thr Phe Tyr Gly Gly Gly Asp Ala
            35                  40                  45

Ser Gly Thr Met Gly Gly Ala Cys Gly Tyr Gly Asn Leu Tyr Ser Ser
            50                  55                  60

Gly Tyr Gly Thr Asn Thr Ala Ala Leu Ser Thr Ala Leu Phe Asn Asn
65                  70                  75                  80

Gly Leu Ser Cys Gly Ser Cys Phe Gln Ile Arg Cys Val Asn Asp Arg
            85                  90                  95

Ser Cys Leu Arg Gly Val Ile Thr Val Thr Ala Thr Asn Phe Cys Pro
            100                 105                 110

Pro Gly Gly Trp Cys Glu Pro Pro Asn Pro His Phe Asp Leu Ser Gln
            115                 120                 125

Pro Val Phe Leu Arg Ile Ala Gln Tyr Arg Ala Gly Val Val Pro Val
            130                 135                 140

Ala Tyr Arg Arg Val Pro Cys Arg Arg Ser Gly Gly Ile Arg Phe Thr
145                 150                 155                 160

Ile Asn Gly His Ala Phe Phe Asn Leu Val Leu Val Thr Asn Val Gly
            165                 170                 175

Gly Ser Gly Asp Val His Ala Val Tyr Ile Lys Gly Ser Arg Thr Gly
            180                 185                 190

Trp Gln Met Met Ser Arg Asn Trp Gly Gln Asn Trp Gln Ser Asn Ala
            195                 200                 205

Asn Leu Asn Gly Gln Ser Leu Ser Phe Arg Val Val Thr Gly Asp Ser
            210                 215                 220

Arg Ser Val Val Ser Tyr Asn Ala Ala Pro Pro Gly Trp Ser Phe Gly
225                 230                 235                 240

Gln Thr Tyr Ser Gly Ala Gln Phe Arg
            245
```